US006153403A

United States Patent [19]
Lim et al.

[11] Patent Number: 6,153,403
[45] Date of Patent: Nov. 28, 2000

[54] LYSOSOMAL-ASSOCIATED MULTISPANNING MEMBRANE PROTEIN, LAPTM5 AND NUCLEIC ACID ENCODING LAPTM5

[76] Inventors: Bing Lim, 4 Hooper St., Dorchester, Mass. 02124; Chaker N. Adra, 1 Devonshire Pl., Apt. 3601, Boston, Mass. 02109

[21] Appl. No.: 08/889,425

[22] Filed: Jul. 8, 1997

Related U.S. Application Data

[60] Provisional application No. 60/021,399, Jul. 9, 1996.

[51] Int. Cl.$^7$ .................................................. C12N 15/12
[52] U.S. Cl. ................... 435/69.1; 435/320.1; 536/23.5; 935/22
[58] Field of Search ........................ 536/23.5; 435/320.1, 435/70.1, 71.1, 69.1, 325; 935/22

[56] References Cited

FOREIGN PATENT DOCUMENTS

WO94/13802  6/1994  WIPO.

OTHER PUBLICATIONS

Nagase et al. (DNA Res. 2(1):37–43) Accession # D42042. Genbank, Nov. 7, 1994.
Campbell, AM. General properties and applications of monoclonal antibodies. in: Monoclonal antibody technology. Elsevier Science Publishers, Amsterdam. pp. 1–32, 1984.
Kornfeld, S. and Mellman, I., "The Biogenesis of Lysosomes," *Annu. Rev. Cell Biol.* 5: 483–525 (1989).
Huang, H. and Auerbach, R., "Identification and Characterization of Hematopoietic Stem Cells From the Yolk Sac of the Early Mouse Embryo," *Proc. Natl. Acad. Sci. USA 90*: 10110–10114 (1993).
Wong, P.M.C. et al., "Properties of The Earliest Clonogenic Hematopoietic Precursors to Appear in the Developing Murine Yolk Sac," *Proc. Natl. Acad. Sci. USA 83*: 3851–3854 (1986).
Adra, C.N, and Lim, B., "Identification of an Embryonic cDNA for a Five–transmembrane Juxtanuclear Protein Preferentially Expressed in Adult Hematopoietic Cells," *Amer. Jour. Human Genetics 57 (4) Suppl.*: A312 (1995).
Ren, R. et al., "Identification of a Ten–Amino Acid Proline–Rich SH3 Binding Site," *Science 259*: 1157–1161 (1993).
Cohen, G.B. et al., "Modular Binding Domains in Signal Transduction Proteins," *Cell 80*: 237–248 (1995).
Cannizzaro, L.A. et al., "Regional Mapping of the Human Galactocerebrosidase Gene (GALC) to 14q31 by in Situ Hybridization," *Cytogenet. Cell Genet. 66*: 244–245 (1994).
Gieselmann, V. et al., "Molecular Genetics of Metachromatic Leukodystrophy," *Hum. Mutat. 4*: 233–242 (1994).
Scriver, C.R. et al., eds. "Lysosomal Enzymes," in *The Metabolic and Molecular Bases of Inherited Disease*, pp 2427–2837, 7th ed., McGraw–Hill, New York (1995).
Ciechanover, A., "The Ubiquitin–Proteasome Proteolytic Pathway," *Cell 79*: 13–21 (1994).
Rock, K.L. et al., "Inhibitors of the Proteasome Block the Degradation of Most Cell Proteins and the Generation of Peptides Presented on MHC Class 1 Molecules," *Cell 78*: 761–771 (1994).
Germain, R.N., "MHC–Dependent Antigen Processing and Peptide Presentation: Providing Ligands for T Lymphocyte Activation," *Cell 76*: 287–299 (1994).
Fields, S. and Song, O., "A Novel Genetic System to Detect Protein–Protein Interactions," *Nature 340*: 245–246 (1989).
Wang, T. et al., "Specific Interaction of Type I Receptors of the TGF–β Family With The Immunophilin FKBP–12," *Science 265*: 674–676 (1994).
Wiborg, O. et al., "The Human Ubiquitin Multigene Family: Some Genes Contain Multiple Directly Repeated Ubiquitin Coding Sequences," *EMBO J. 4*: 755–759 (1985).
Baker, R.T., and Board, P.G., "The Human Ubiquitin Gene Family: Structure of a Gene and Pseudogenes from the Ub B Subfamily," *Nucleic Acids Res. 15*: 443–463 (1987).
Einspanier, R. et al., "Cloning and Sequence Analysis of a cDNA Encoding Poly–ubiquitin in Human Ovarian Granulosa Cells," *Biochem. Biophys. Res. Commun. 147*: 581–587 (1987).
Doherty, F.J. et al.,"Ubiquitin–protein Conjugates Accumulate in the Lysosomal System of Fibroblasts Treated with Cysteine Proteinase Inhibitors," *Biochem. J. 263*: 47–55 (1989).
Schwartz, A.L. et al., "Immunoelectron Microscopic Localization of the Ubiquitin–activating Enzyme E1 and HepG2 Cells," *Proc. Natl. Acad. Sci. USA 89*: 5542–5546 (1992).
Azorsa, D.O. et al., "CD63/Pltgp40: A Platelet Activation Antigen Identical to the Stage–specific, Melanoma–associated Antigen ME491," *Blood 78*: 280–284 (1991).
Fields, S. and Sternglanz, R., "The Two–Hybrid System: An Assay for Protein–Protein Interactions," *TIG 10(8)*: 286–292 (1994).
Midgley, C.A. and Lane, D.P., "Looking for Protein–Protein Interactions," in *Cellular Interactions in Development: A Practical Approach* (Hartley, D.A., ed.) 129–151, Oxford Univ. Press, Oxford, U.K. (1993).
Adra, C.N. et al., "LAPTM5: A Novel Lysosomal–Associated Multispanning Membrane Protein Preferentially Expressed in Hematopoietic Cells," *Genomics 35*: 328–337 (1996).
Nagase, T. et al., "Prediction of the Coding Sequences of Unidentified Human Genes. III. The Coding Sequences of 40 New Genes (KIAA0081–KIAA0120) Deduced by Analysis of cDNA clones from Human Cell Line KG–1," *DNA Research 2*: 37–43 (1995).

(List continued on next page.)

*Primary Examiner*—Christina Y. Chan
*Assistant Examiner*—F. Pierre VanderVegt
*Attorney, Agent, or Firm*—Hamilton, Brook, Smith & Reynolds, P.C.

[57] ABSTRACT

This invention relates to the discovery of a novel nucleic acid molecule which encodes a hematopoietic-specific protein, termed LAPTM5. The expression pattern of the gene together with evidence that the protein interacts with ubiquitin indicates that the protein has a functional role during embryogenesis and in adult hematopoietic cells.

3 Claims, 4 Drawing Sheets

OTHER PUBLICATIONS

Scott, L.M. et al., "E3, A Hematopoietic–specific Transcript Directly Regulated by the Retinoic Acid Receptor Alpha," EMBL Database entry MM29539; Accession No. U29539 (1995).

Scott L.M., "Human Retinoic–acid Inducible E3 Protein mRNA, Complete Coding Sequence," EMBL Database entry HS304981; Accession No. U30498 (1995).

Scott, L.M. et al., "E3, A Hematopoietic–specific Transcript Directly Regulated by the Retinoic Acid Receptor Alpha," *Blood 88*: 2517–2530 (1996).

Gropper, R. et al., "The Ubiquitin–activating Enzyme, E1, is Required for the Stress–induced Lysosomal Degradation of Cellular Proteins," *J. Biol. Chem. 266*: 3602–3610 (1991).

Lelias, J–M. et al., "cDNA Cloning of a Human mRNA Preferentially Expressed in Hematopoietic Cells and With Homology to a GDP–dissociation Inhibitor for the rho GTP–binding Proteins," *Proc. Natl. Acad. Sci. USA 90*: 1479–1483 (1993).

Adra, C.N. et al., "Identification of a Novel Protein with GDP Dissociation Inhibitor Activity for the Ras–like Proteins CDC42Hs and Rac 1," *Genes Chromosomes Cancer 8*: 253–261 (1993).

Adra, C.N. et al., "Assignment of the Human GDID4 Gene, a GDP/GTP–Exchange Regulator, to Chromosome 12p12.3," *Genomics 24*: 188–190 (1994).

Goldberg, A.L. and Rock, K.L., "Proteolysis, Proteasomes and Antigen Presentation," *Nature: 357*: 375–379 (1992).

Dice, J.F., "Peptide Sequence that Target Cytosolic Proteins for Lysosomal Proteolysis," *Trends Biochem. Sci. 15*: 305–309 (1990).

Lenk, S.E. et al., "Ubiquitin–activating Enzyme, E1, is Associated with Maturation of Autophagic Vacuoles," *J. Cell Biol. 118*: 301–308 (1992).

Yewdell, J. et al., MHC–encoded Proteasome Subunits LMP2 and LMP7 are Not Required for Efficient Antigen Presentation, *J. Immunol. 152*: 1163–1170 (1994).

FIGURE 1

```
                    10           20           30          40         50
human     MDPRLSTVRQTCCFNVRIATTALAIYHVIMSVLLFIEHSVEVAHGKASC
          | * | ** |||||||||| * | * ||   ||||||** ||||||||| |||| * ||   ||
mouse     MASRAAPVRQTCCFNIRVATIALAIYHIVMSVLLFIEHVVEVARGKVSC
                    60           70          80          90        100
human     KLSQMGYLRIADLISSFLLITMLFIISLSLLIGVVKNREKYLLPFLSLQI
          *   | * ||| * ||||||||| ** ||||| * |||  ||||||||| * ||||||||
mouse     RFFKMPYLRMADLLSSFLLIGVLFIISISLLFGVVKNREKYLIPFLSLQI
                   110          120         130         140        150
human     MDYLLCLLTLLGSYIELPAYLKLASRSRASSSKFPLMTLQLLDFCLSILT
          || * ||||||||||||||||||||| * | *** || |||||||||||||||||
mouse     MDFLLCLLTLLGSYIELPAYLKLA.RPRPGPSKVPLMTLQLLDFCLSILT
                   160          170         180         190        200
human     LCSSYMEVPTYLNFKSMNHMNYLPSQEDMPHNQFIKMMIIFSIAFITVLI
          |||||||||||||||||||||||||||||||| * ||| || * ||| * ||||||||
mouse     LCSSYMEVPTYLNFKSMNHMNYLPSQEGVPHSQFINMMLIFSVAFITVLI
                   210          220         230         240        250
human     FKVYMFKCVWRCYRLIKCMNSVEEKRNSKMLQKVVLPSYEEALSLPSKTP
          ||||||| * || * *| |||   |||  || ||||||||||| * |||
mouse     LKVYMFKCVYTCYKFLKHMNSAMEDSSSKMFLKVALPSYEEALSLPPKTP
                   262
human     EGGPAPPPYSEV
          || * ||||||||||
mouse     EGDPAPPPYSEV
```

FIGURE 2

```
CGGTGCTTTGGGCCCAAGACTCCTTACTCAGAGCCTCCGAAGAGAGGGACTGCGCACCATGGCCTCCCGTGCAGCGCCGGTCAGACAGACA
----------+---------+---------+---------+---------+---------+---------+---------+---------+   90
GCCACGAAACCCGGGTTCTGAGGAATGAGTCTCGGAGGCTTCTCCCCTGACGCGTGGTACCGGAGGCACGTCGCGGCCAGTCTGTCTGT

TGCTGTTGTTTCAACATCCGAGTCGCCACCATAGCCCTGGCCATTTACCACACATGAGTGTCCTGCTGTTCATTGAGCATGTGGTG
----------+---------+---------+---------+---------+---------+---------+---------+---------+  180
ACGACAACAAAGTTGTAGGCTCAGCGGTGGTATCGGGACCGGTAAATGGTGTATCAGTACTCACAGGACGACAAGTAACTCGTACACCAC

GAGGTGGCCCGCGGTAAAGTGTCCTGTAGGTTCTTCAAGATGCCGTACCTCAGGATGGCTGACCTTCTCTCCAGCTTCCTGCTCATTGGC
----------+---------+---------+---------+---------+---------+---------+---------+---------+  270
CTCCACCGGGCGCCATTTCACAGGACATCCAAGAAGTTCTACGGCATGGAGTCCTACCGACTGGAGTACCTGATACCCTTCCTGTCCCTTCAAATCATG

GTGCTCTTCATCATCAGCATGCCTGCTGTTCGGCGTGGTCAAGAACCGGGAGAAGTACCTGATACCCTTCCTGTCCCTTCAAATCATG
----------+---------+---------+---------+---------+---------+---------+---------+---------+  360
CACGAGAAGTAGTAGTCGGACGACAAGCCGCCACCAGTTCTTGGCCCTCTACACTGCAGCGTACTTGAAGCTTGCCCGGCCCTGGTCCTTCT

GACTTCCTGCTCTGCCTGCTCACACTGCTGGGCTCCTACACTCGAATTGCCAGCGTACTTGAAGCTTGAACGGTCGCATGAACTTCGACCCTC
----------+---------+---------+---------+---------+---------+---------+---------+---------+  450
CTGAAGGACGAGACGACGAGTGTGACGACCCGAGGATGTAGCTTAACGGTCGCATGAACTTCGACCCTGTGCAGCTCGTGACCTCGAGGAAGA

AAGGTCCCCTTGATGACACTGCTAGACTTCTGTTTGAGTATCCTGACCGTCGTGCAGCTCGTGACCTGGGACACGTCGAGGATGTACCTTCACGGGTGGATGGAG
----------+---------+---------+---------+---------+---------+---------+---------+---------+  540
TTCCAGGGGAACTACTGTGACGTCGACGATCGAAGACAAACTCATAGGACTGCTGTCCCAAGCCAGGAGGGTGTGCCGCACAGCCAGTTCATCAACGATGCTCATCTCTCA

AACTTCAAGTCCATGAACCATGGTACTTGGTGTACTTAATGAGGACTTGTACTAGCACCATGTGTACACATGTGTACGATGTGTTTAAGAACTTCGTGTACTTAAGCCGG
----------+---------+---------+---------+---------+---------+---------+---------+---------+  630
TTGAAGTTCAGGTACTTGGTGTACTTAATGAGGACTTGTACTAGCACCATGTGTACACATGTGTACGATGTGTTTAAGAACTTCGTGTACTTAAGCCGG

GTGGCCCTTTATCACCGTGCTCATCCTGAAGGTCTACATGTTCAAGTGTGTACACATGTGTACACACATGTGTACGATGTGTTTAAGAACTTCGTGTACTTAAGCCGG
----------+---------+---------+---------+---------+---------+---------+---------+---------+  720
CACCGGGAAATAGTGGCACGAGTAGGACTTCCAGATGTTCCTCAAGGAGTTCCACCGAGACGCAGGAGCCTTGTCCTTCCGAACAGAGACGGGGATTCTGAGGTCTCCC

ATGGAGGACAGCAGTCTCGTGGAGTTCTACAAGGAGACTTGTTCCTCAAGGAGTTCCACCGAGACGCAGGAGCCTTGTCCTTCCGAACAGAGACGGGGATTCTGAGGTCTCCC
----------+---------+---------+---------+---------+---------+---------+---------+---------+  810
TACCTCCTGCTCGTGTCGAGAGTTCATACAGGTGTGATCCCACACTAGGGGTGGTCCGGAAATCGGGAACCCGACCCTCTCCGGAAGGAGGACGAA

GACCCTGCACCTGGGGTATGAGTCTTCACACTAGGGGTGGTCCGGAAATCGGGAACCCGACCCTCTCCGGAAGGAGGACGAA
----------+---------+---------+---------+---------+---------+---------+---------+---------+  900
CTGGGACGTGTGGGGTTGCTGTGGCCTGCTACAGGACAATCTGCTTGTGCCCCCCACTGCTTCCTCCTCGGGGACCCTCAC

CTTCACTTTGGTGGTTGCTGTGGCCTGCTACAGGACAATCTGCTTGTGCCCCCCACTGCTTCCTCCTCGGGGACCCTCAC
----------+---------+---------+---------+---------+---------+---------+---------+---------+  990
GAAGTGAAACCACCAACGACCGGACGATGTCCTGTTAGACGAACACGGGGGAGTGACAGGAGAACACGGGGGAGTGACAGGAGAGAGCCCTGGGAGTG

FIGURE 3A
```

```
TCACAACTGAGTCACCCTGGGCTCAGTGACCCTTTGCGGGCTCAGGATACTCAGCCTAGCAGCCCGTCTCGTCTCCATCAGCAGTGACACT
       +         +         +         +         +         +         +         +         +         1080
AGTGTTGACTCAGTGGGACCCGAGTCACTGGGAAACGCCGAGTCCTATGAGTCGGATCGTCGGGCAGAGCAGAGGTAGTCGTCACTGTGA

TGTTCAGAGCGCAGCCATAGGAAGTTAGGGTGCGTTTGGTTAACAGCTACCGGCTTGTCTGTTTGGCCAGGCAGCAGCAGGAAGAGAAT
       +         +         +         +         +         +         +         +         +         1170
ACAAGTCTCGCGTCGGTATCCTTCAATCCCACGCAAACCAATTGTCGATGGCGAACTAGACAAACCGGTCCGTCGTCGTCCTTCTCTTA

CTGGCCAAGCAATAGTTCCTGGTGTCAGTTTATACTCAGTCTGTCAGACGACAGGATGGGTCATGATTGTTGTGCCCGTTTGCCACCTCCA
       +         +         +         +         +         +         +         +         +         1260
GACCGGTTCGTTATCAAGGACCACAGTCAAATATGAGTCAGACAGATGAGCTGATCACCAGTACTAACACCAGGGCAAACGGTGGAGGT

GTACCCCAAAAGTGTACAAACAAAACAATTCCTTCAAATAGCTTGCTTAAATAGCGATTCAGCCCCGGAATTC
       +         +         +         +         +         +         +         → 1333
CATGGGGTTTTCACATGTTTGTTTTGTTAAGGAAGTTTATCGAACGAATTTATCGCTAAGTCGCTAAGTCGGGGCCCTTAAG
```

FIGURE 3B

LYSOSOMAL-ASSOCIATED MULTISPANNING MEMBRANE PROTEIN, LAPTM5 AND NUCLEIC ACID ENCODING LAPTM5

RELATED APPLICATIONS

This application claims priority to U.S. Provisional Application Ser. No. 60/021,399, filed Jul. 9, 1996, the contents of which are incorporated herein by reference in its entirety.

GOVERNMENT FUNDING

This invention was made with Government support from the National Institute of Health under Grant DK44099. The Government has certain rights in the invention.

BACKGROUND OF THE INVENTION

The hematopoietic system is characterized by a phenotypic and functional diversity of multiple lineages derived from a common stem cell. Different classes of genes that are critical for the development, proliferation, and function of stem cells, progenitor cells and terminally differentiated lineages have thus far been recognized. These include transcriptional factors (Ness, S. A. and Engel, J. D., Curr. Opin. Genet. Dev. 4:718–724 (1994); Dorshkind, K., Cell 79:751–753 (1994); Scott, E. W. et al., Science 265:1573–1577 (1994)), an array of signaling molecules such as kinases and phosphatases (Hunter, T., Cell 80:225–236 (1995); Taniguchi, T., Science 288:251–255 (1995); Schulz, L. D. et al., Cell 73:1445–1454 (1993)), adhesion molecules (Clark, E. A. and Brugge, J. S., Science 268:233–239 (1995)), and an increasingly complex network of cytokines and cytokine receptors (Kishimoto, T. et al., Cell 76:253–262 (1994); Ihle, J. N. et al., Annul Rev. Immunol. 13:369–398 (1995)). A need exists to further identify hematopoietic-specific proteins and their functions.

SUMMARY OF THE INVENTION

This invention relates to the discovery of a novel nucleic acid molecule which encodes a hematopoietic-specific protein, termed LAPTM5. As such, the invention relates to and includes, for example, an isolated nucleic acid molecule which codes for a LAPTM5 protein or a fragment or mutant thereof or hybridizes to a nucleic acid coding for LAPTM5 (such as the sequences in FIGS. 1 and 2), or a fragment or a complement thereof.

The invention further relates to plasmids containing these nucleic acid molecules operably linked to a promoter, a process for manufacturing or isolating LAPTM5 protein and LAPTM5 proteins and fragments thereof. In another embodiment, the invention relates to antibodies which selectively bind to the protein.

In yet another embodiment, the invention relates to the use of these nucleic acids, proteins and antibodies as probes and/or in assays.

DESCRIPTION OF THE DRAWINGS

FIG. 1 is a nucleotide (SEQ ID NO:1) and deduced amino acid sequence (SEQ ID NO:2) of full-length human LAPTM5 cDNA. The amino acid sequence of the longest open reading frame is numbered to the right beginning with the first presumed initiating methionine. A TGA stop codon (***) is followed by a long 3'-untranslated region containing an AATAAA polyadenylation signal (double underlined). The five putative transmembrane domains are underlined. The carboxyl-terminal peptide (residues 247–262) used in generating the antibody is boxed.

FIG. 2 is an alignment of the amino acid sequences of human (SEQ ID NO:2) and murine (SEQ ID NO:4) LAPTM5 proteins. A gap between murine residues is marked by a dot. Identical residues are aligned with vertical bars and conserved residues with asterisks (*) following the groupings: S, T, G, A, P; L, M, I, V; E, D, Q, N; R, H, K; and F, Y, W. The five putative transmembrane domains are boxed.

FIGS. 3A & 3B are the murine cDNA sequence (SEQ ID NO:3) encoding murine LAPTM5 protein (SEQ ID NO:4).

DETAILED DESCRIPTION OF THE INVENTION

As set forth above, the invention relates to the discovery and isolation of a nucleic acid molecule and protein which are expressed selectively in hematopoietic tissue. Using a subtractive hybridization strategy between hematopoietic and nonhematopoietic cells, a cDNA was cloned. The cDNA codes for a multitransmembrane protein that is preferentially expressed in hematopoietic tissues and localized to lysosomes. Intraluminal lysosomal enzymes are critical for the proteolytic degradation and processing of cellular proteins (Kornfeld, S. and Mellman, I., Annu. Rev. Cell Biol. 5:483–525 (1989)). Its expression pattern also suggests an organelle protein of specialized function in hematopoietic cells.

The novel protein has several interesting and unique characteristics. The expression of the gene in embryonic totipotent stem cells and in tissues from every part of Day 11 postcoitus (p.c.) embryos supports the conclusion that the protein is important during early embryonic development. In view of the results obtained in a Southern analysis of a zoo blot of DNA from other species, the gene is conserved across evolution in mammals (including humans and mice) and lower species such as fish. With maturation into the adult animal, there is a switch to a preferential expression of the transcript in hematopoietic tissues (thymus, spleen, lymph node, and bone marrow). This switch supports the conclusion that the protein performs a function of particular importance in adult hematopoietic cells. During embryogenesis, the spatial reorganization of tissues and development of organs at specific sites presumably involve a large turnover of cells. Similarly, in the adult hematopoietic system, unlike embryonic hematopoiesis, a high turnover and continuous replacement of terminally differentiated cells are required. It is believed that the protein functions to serve this common requirement of turnover of cells.

Among the immortalized cell lines examined thus far, the RNA transcript has only been observed in hematopoietic lines. The spectrum of cell lines analyzed includes erythroid, granulocytic, megakaryocytic, and B- and T-lymphocytic cells. Normal cell populations enriched for neutrophils, macrophages, mast cells, and eosinophils also express the mRNA and protein. In normal mouse tissues the mRNA is easily detected in hematopoietic tissues (thymus, spleen, lymph node, and bone marrow) but is absent or hardly detectable in a spectrum of nonhematopoietic tissue. More sensitive analysis of poly(A)$^+$ RNA from human tissues revealed the same high level of preferential expression in hematopoietic tissues and at lower levels in some nonhematopoietic tissues. It is possible that transcripts detected in other nonhematopoietic tissues, such as lung, may be from contaminating hematopoietic cells such as alveoli macrophages.

To investigate the relevance of LAPTM5 to hematopoietic cells further, its expression during induced differentiation of yolk sac cells was examined. The high level of embryonic βh1 globin in the total RNA of Day 9.5 p.c. yolk sac cells is consistent with data showing that the predominant cells in the yolk sac are primitive large nucleated erythroid cells (Metcalf, D. and Moore, M. A. S., "Embryonic aspects of hemopoiesis," in *Hematopoietic Cells* pp. 172–266, North Holland, Amsterdam (1971)). The decrease in βh1-globin in later colonies reflects a combination of the emergence of erythroid cells with adult hemoglobin (Wong, P. M. C. et al., *Proc. Natl. Acad. Sci. USA* 83:3851–3854 (1986)), the shorter survival of erythroid colonies in culture, and a predominance of myeloid colonies by Day 6. Precursors for other hematopoietic lineages, including adult erythrocytes and myeloid and lymphoid cells, have been identified in yolk sac cells (Wong, P. M. C. et al., *Proc. Natl. Acad. Sci. USA* 83:3851–3854 (1986); Cumano, A. et al., *Proc. Natl. Acad. Sci. USA* 90:6429–6433 (1993); Liu, C. P. and Auerbach, R., *Development* 113:1315–1323 (1991); Huang, H and Auerbach, R., *Proc. Natl. Acad. Sci. USA* 90:10110–10114 (1993)). The culture assay used herein permitted the development of erythroid, macrophage, granulocytic, and mixed-lineage colonies of adult hematopoietic cell characteristics (Wong, P. M. C. et al., *Proc. Natl. Acad. Sci. USA* 83:3851–3854 (1986); Metcalf, D. and Moore, M. S. A., "Embryonic aspects of hemopoiesis," in *Hematopoietic Cells* pp. 172–266, North Holland, Amsterdam (1971)). Thus, the total RNA from pooled colonies represents differentiated cells originating from yolk sac clonogenic precursors. Day 9.5 yolk sac cells expressed only a very low level of LAPTM5 mRNA, compared to that of embryonic erythroid cells (Wong, P. M. C. et al., *Proc. Natl. Acad. Sci. USA* 83:3851–3854 (1986)). However, upon differentiation into hematopoietic colonies, there is a significantly higher level of LAPTM5 mRNA in differentiated cells from colonies as early as Day 2, indicating that the gene has been up-regulated in cells of adult hematopoiesis. The overall pattern of expression of the gene thus suggests that the protein is of particular importance in adult hematopoietic tissues.

The 29-kDa protein (p29) detected by Western blot analysis is consistent with the estimated weight based on total amino acids. No proteins of other molecular weights were detected, indicating that the protein does not undergo post-translational modifications, such as glycosylation.

p29/LAPTM5 has no homology to any of the lysosomal proteins, which are all highly glycosylated. In the carboxyl terminus there is a stretch of about 13 amino acids rich with prolines (PXXXPXXXPXPPP) (SEQ ID NO:6), conserved between the human and murine proteins (FIG. 2). Several proteins with proline-rich domains have been found to be involved in interaction with SH3 domain-containing proteins (Ren, R. et al., *Science* 259:1157–1161 (1993); Cohen G. B. et al., *Cell* 80:237–248 (1995)). A proline-rich motif has also been identified in ion channels (Rotin, D. et al., *EMBO J.* 13:4440–4450 (1994)). The proline-rich region in the LAPTM5 protein, highly conserved between human and murine protein, is believed to be a domain of functional significance.

The computer prediction that the protein is a highly hydrophobic 5-transmembrane protein indicates that the protein is located either in the cell membrane or in an intracellular membrane compartment. Immunofluorescent studies of cells in steady-state reveal an intracellular protein. The dominant juxtanuclear staining in a crescent-shape pattern indicates that p29 is likely to be present primarily in or around the Golgi apparatus. Two-color immunofluorescent analysis with the AD7 antibody, specific for a 200-kDa protein in the Golgi (Narula, N. et al., *J. Cell Biol.* 117:27–38 (1992)), shows that the p29/LAPTM5 protein is dispersed outside of the bulk of the Golgi stack, but it cannot entirely be ruled out that there is an association with the Golgi such as in the trans-Golgi network. Thus far, p29 colocalizes best with all three antibodies that detect the lysosomal proteins, the major glycoproteins LAMP-1 and LAMP-2, and the CD63 protein. Western analysis of cell fractions from rat spleen confirmed the presence of the protein in lysosomes. Localization of LAPTM5 in hematopoietic cells was established by indirect immunofluorescence microscopy. Electron microscopy studies together with ongoing studies to examine the pattern of distribution of p29 upon cell activation or the effect of treatment with organelle membrane-altering agents such as Brefeldin A (Klausner, R. D. et al., *J. Cell Biol.* 116:1071–1080 (1992)) should yield more definitive data about the distribution and movement of the LAPTM5 protein. Nevertheless, the preliminary localization data point to a protein concentrated in lysosomal organelles during steady-state.

The gene maps to human chromosome 1p34, a region that has thus far not been linked with known lysosomal disorders (Cannizzaro, L. A. et al., *Cytogenet. Cell Genet.* 66:244–245 (1994); Gieselmann, V. et al., *Hum. Mutat.* 4:233–242 (1994); Scriver, C. R. et al., "Lysosomal Enzymes" in *The Metabolic and Molecular Bases of Inherited Diseases*, pp. 2427–2839, 7th ed., McGraw-Hill, New York (1995)).

The localization of LAPTM5 to lysosome and lysosome-related compartments suggests interesting possibilities about the function of this gene. Lysosomal and ubiquitin pathways together constitute the major proteolytic system in mammalian cells (Kornfeld, S. and Mellman, I., *Annu. Rev. Cell Biol.* 5:483–525 (1989); Ciechanover, A. *Cell* 79:13–21 (1994); Goldberg, A. L. and Rock, K. L. , *Nature* 357:375 (1992)). Cellular proteins exist in a dynamic state of synthesis and degradation essential for maintaining homeostasis and for regulating levels of critical proteins in metabolic and differentiation pathways. Protein degradation is finely controlled, such as the level of oncoproteins p53, c-myc, c-fos, and E1A or the cell-cycle proteins cyclin A and B (Ciechanover, A., *Cell* 79:13–21 (1994)). These are ubiquitin-mediated proteolyses that occur in cytosolic proteosomes but there is evidence that some may be linked to lysosomal pathways (Ciechanover, A., *Cell* 79:13–21 (1994); Doherty, F. J. et al., *Biochem. J.* 263:47–55 (1989); Dice, A. F., *Trends Biochem. Sci.* 15:305–309 (1990)). For example, while recent findings have shown that the ubiquitin/proteosome complex is essential and critical for processing of MHC-restricted class 1 antigens (Rock, K. L. et al., *Cell* 78:761–771 (1994)), it is believed that lysosomes also participate in this function (Lenk, S. E. et al., *J. Cell Biol.* 118:301–308 (1992); Yewdell, J. et al., *J. Immunol.* 152:1163 (1994)). In addition, intraluminal lysosomal enzymes are critical for the proteolytic degradation and processing of proteins (Kornfeld, S. and Mellman, I. *Annu. Rev. Cell Biol.* 5:483–525 (1989)). These proteins likely include those responsible for ATP-dependent acidification and transmembrane transport of amino acids, fatty acids, carbohydrates, and nutrients such as cholesterol and cobalamin (Kornfeld, S. and Mellman, I. *Annu. Rev. Cell Biol.* 5:483–525 (1989)). Many of the lysosomal membrane proteins may be transporters or channel proteins. Others, like the tetraspanning melanoma-associated antigen CD63/ME491, are mobilized to the cell surface upon activation and are thought to play a role in cell adhesion and tumor metastasis (Azorsa, D. O. et al., *Blood* 78:280–284 (1991)). Finally, lysosomes are also involved in the modification of protein prior to antigen presentation (Germain, R. N., *Cell* 76:287–299 (1994); Rudensky, A. Y. et al, *Immunity* 1:585–594 (1994)).

Therefore, it is most interesting that from our screening of a yeast cDNA library, using the proline-rich carboxyl tail of the LAPTM5 protein as bait in the double-hybrid yeast system (Fields, S. and Song, O., *Nature* 340:245–246 (1989); Wang, T. et al., *Science* 265:674–676 (1994)), three different cDNAs encoding putative LAPTM5-interacting proteins have been isolated. Surprisingly, all three are cDNAs coding for fusion proteins that are precursors of ubiquitin (Wiborg, O. et al., *EMBO J.* 4:755–759 (185) Baker, R. T. and Board, P. C., *Nucleic Acids Res.* 15:443 463 (1987); Einspanier, R. et al., *Biochem. Biophys. Res. Commun.* 147:581–587 (1987)). The significance of this is underscored by the fact that ubiquitinated protein conjugates have been detected in lysosomes of fibroblasts (Doherty, F. J. et al., *Biochem. J.* 263:47–55 (1989); Schwartz, A. L. et al., *Proc. Natl. Acad. Sci. USA* 89:5542–5546 (1992)), which leads to the suggestion that some ubiquitin-protein conjugates may normally be degraded lysosomally (Cropper, R. et al., *J. Biol. Chem.* 166:3602–3610 (1991)) and implies that protein ubiquitination may serve as a signal for protein uptake in the lysosomal system. Our finding of the interaction of LAPTM5 with ubiquitin supports the conclusion that LAPTM5 mediates the degradation of ubiquitinated proteins in lysosomes.

As such, a gene, LAPTM5, located at chromosome 1p34, was identified that encodes a novel 5-transmembrane protein that is stage and tissue specific. p29/LAPTM5 represents the rare organelle proteins that are preferentially expressed in a particular tissue type, in this case hematopoietic tissues. The localization of the protein predominantly to lysosomes and binding to ubiquitin has been observed. The conservation of LAPTM5 across evolution suggests that the gene serves a basic cellular function. The preferential expression of LAPTM5 in adult hematopoietic tissues points to a protein of particular relevance to hematopoietic cells. The available reagents should also be useful in the physiological investigations of intracellular organelles.

The LAPTM5 protein, as defined herein, encompasses a nucleic acid expression product which possesses one or more of the functions of a native LAPTM5 protein. A "native protein" is defined as a protein which is encoded by a nucleic acid which is, or is capable of being, obtained from a nucleic acid library of a cell or cells. Allelic variants of a protein are, for example, considered "native proteins". Native proteins include proteins which are directly obtained from a hematopoietic cell, for example by isolation, as well as proteins which are produced recombinantly or synthetically in a hematopoietic cell or in a non-hematopoietic cell. The native protein, or a nucleic acid encoding the protein, can be of animal origin, including vertebrates such as reptiles, birds, fish, or mammals such as humans.

LAPTM5 proteins, as defined herein, also include functional protein or polypeptide fragments of the native protein and/or proteins or polypeptides where one or more amino acids have been deleted, added or substituted. "Homology" is defined herein as sequence identity. Preferably, the protein or polypeptide shares at least about 50% sequence identity or homology and more preferably at least about 75% identity or at least about 90% identity with the corresponding sequences of the native protein, for example, with FIG. 2. For example, the derivative, mutant or variant can possess substantially the same amino acid sequence as the native protein. In one embodiment, the amino acids which are deleted, added or substituted are amino acids which are not "conserved" between species, as identified in a sequence alignment exemplified in FIG. 2. Conserved amino acids may also be substituted, but are preferably substituted conservatively or substituted by structurally similar amino acids. Conservative substitutions include amino acid substitutions within the following the groupings: S, T, G, A, P; L, M, I, V; E, D, Q, N; R, H, K; and F, Y, W. An example of a suitable derivative or mutant of the LAPTM5 protein is a protein possessing a consensus sequence of the originating species.

A "functional" fragment, derivative, mutant, or allelic variant is of sufficient length and/or structure as to possess one or more biological activities of the protein. One example of such a biological activity of the protein is antigenic or immunogenic activity. In this embodiment, it is preferred that the fragment or derivative conserve one or more portions of the protein which do not reside within a membrane (e.g., transmembrane sequences). In another embodiment, the protein derivative is conserved within the transmembrane regions but is lacking in or mutated within one or more exposed regions (e.g., sequences not within the membrane). Examples of suitable fragments include the antigenic carboxyl terminus, as illustrated herein, or an antigenic subfragment thereof. Another example includes the proline-rich region described below. Yet other examples include native LAPTM5 with one or more of these regions removed.

In yet another embodiment, the biological activity of the protein is the ability to bind ubiquitin. The fragment or portion of the protein which binds ubiquitin can be readily determined by preparing mutants or fragments of the protein (such as derivatives which delete or possess amino acid sequences which reside inside or outside of the lysosome or in the transmembrane region) and screening for those which bind and do not bind ubiquitin.

Fragments of the protein can possess at least about 10 amino acids, preferably at least about 20 amino acids. In other embodiments, the fragment possesses essentially all of the amino acids of the full length protein (e.g., at least about 85%, or at least about 95%).

Fusion proteins are intended to be included within the definition of derivatives and can be made by linking one or more amino acids or peptides to the LAPTM5 protein or fragment through a peptide bond. As such, derivatives, such as fusion proteins, can comprise the amino acid sequence of a given protein, such as a native protein. Fusion proteins can be conveniently made through known methods, such as recombinantly. The term derivative is also intended to include proteins which have been labeled, such as a radioactive or calorimetric label. Such derivatives have the improvement to be readily detected in an assay. Yet other fusion proteins are proteins which consist essentially of the amino acid sequence of a given protein (e.g., possess the relevant sequence and, optionally, other amino acids residing at the termini which do not significantly alter or detract from the properties of the protein).

The proteins or fragments can be isolated from the hematopoietic cell of origin or produced synthetically or recombinantly. In a preferred embodiment, the protein is isolated to the substantial absence of conspecific proteins. A conspecific protein is a protein other than LAPTM5 which can be obtained from the cell of origin for the protein or its nucleic acid. The proteins (and nucleic acids) described herein can be preferably isolated, by known methods, to a purity of at least about 50% by weight, more preferably at least about 75% and most preferably to substantial homogeneity. "Substantial homogeneity" refers to the substantial absence of conspecific proteins.

Figure 1:
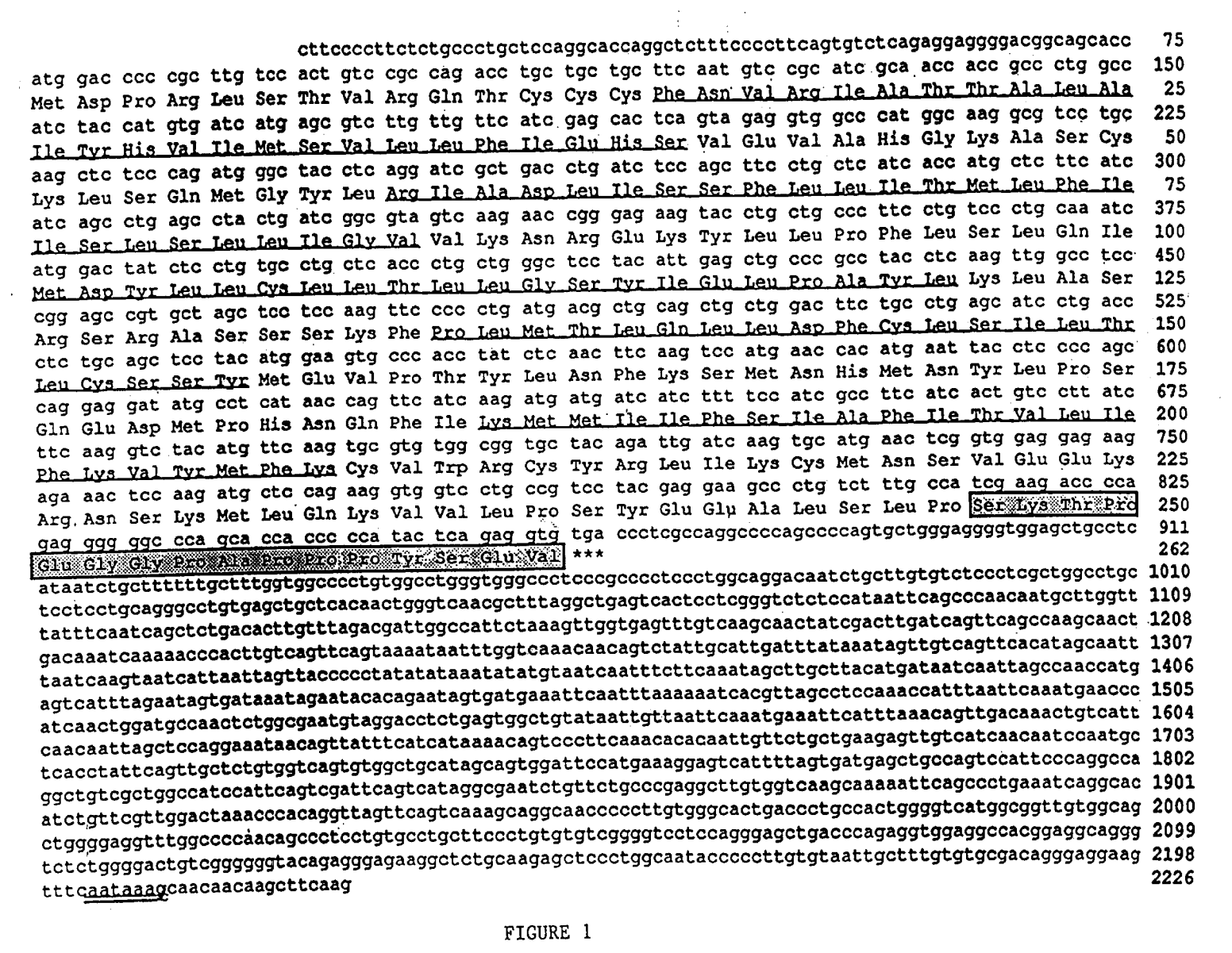

Recombinant or isolated nucleic acid molecules of the invention, in one embodiment, encode a LAPTM5 protein (including the e.g., native proteins, fragments, derivatives, mutants and allelic variants), as defined herein. The molecules can be DNA (including cDNA and genomic DNA) or RNA. In one embodiment, the molecule shares at least about 50% sequence identity, and preferably at least about 75% identity (such as at least about 90% identity) with the corresponding sequences (such as the coding region) of the native gene, particularly in highly conserved regions of the 5-transmembrane protein family. Preferably, the nucleic acid molecule comprises the corresponding coding nucleotide sequence of FIG. 1 or substantially the same sequences thereof, or the complement thereof. As with the proteins above, the nucleic acids can encode proteins which are coded by nucleic acids which are isolated or are capable of being isolated from a nucleic acid library (e.g., "native nucleic acids"). The nucleic acid molecules can hybridize to native nucleic acids, such as the human or murine sequences described herein, under low, medium or high stringency conditions or a stringency which results in the selective isolation of the nucleic acid from a library. The following table provides an example of each condition of stringency.

| Stringency | % Allowed mismatch | ° C. Temperature | % Formamide |
|---|---|---|---|
| High | 6.6 | 52 | 50 |
| Medium | 13 | 45 | 50 |
| Low | 27 | 45 | 22 |

"Selective isolation", or "selective hybridization", is defined herein as embracing the isolation of a sufficiently few number of molecules (preferably one) as to readily permit the identification of the nucleic acid of interest.

In another embodiment the nucleic acid molecules can be employed, for example, as probes to isolate the nucleic acid exemplified herein or related nucleic acids or genes encoding homologous transmembrane proteins, such as homologs of other species or allelic variants. Such molecules comprise recombinant DNA molecules which hybridize to all of or a fragment of the sequences of FIG. 1 (SEQ ID NO:1). Preferably, the molecules hybridize selectively, such as under medium or high stringency conditions, e.g., as set forth in Sambrook et al. *Molecular Cloning: A Laboratory Manual,* 2nd Edition (Cold Spring Harbor Lab., Cold Spring Harbor, N.Y. (1989)).

In yet another embodiment, the invention relates to the use of the probe as a chromosomal marker, as described above, permitting the accurate location of other genes within chromosome, particularly near location 1p34. Such nucleic acids should, again, hybridize selectively, such as under medium or high stringency conditions, to the chromosome of the animal. It is noted that such a nucleic acid need not actually be required to express functional protein.

The nucleic acid molecules can contain coding and non-coding sequences. Preferably, the molecules comprise at least about 25 nucleotides and more preferably at least about 60 nucleotides with 95–100% identity to pull out the LAPTM5 gene or a homolog of the gene. Preferably, the nucleic acid molecule comprises sequences the same as or homologous to the corresponding region encoding the N- or C-termini of the protein. Of course, such molecules need not possess the ability to express functional protein when presented in a cell.

The nucleic acid molecules of the invention preferably possess the ability to express protein, preferably functional, in a cell when operably linked to a suitable regulatory or promoter sequence. As such, the invention includes plasmids and recombinant host cells which contain the nucleic acid molecule under control of such a regulatory sequence. Suitable host cells can be animal (preferably mammals, such as human, murine, rat, rabbit, etc.), plant, bacteria or yeast. Transformation or transfection and expression of cells with heterologous DNA, and recovery of protein, is well described in the Sambrook and Maniatis references cited above.

The LAPTM5 nucleic acids and proteins can also be useful in the research and study of lysosomal proteins, and the binding and function of ubiquitin or ubiquitinated protein. As such, the gene and protein can be useful in, for example, the identification and design of compounds which can block, inhibit or increase ubiquitin binding or ubiquitinated protein binding. In one embodiment, LAPTM5 protein or a cell which expresses LAPTM5 protein is contacted with ubiquitin or ubiquitinated protein. A compound to be assayed is then contacted with the protein and ubiquitin or ubiquitinated protein. The presence or absence of binding can then be detected. Detection can be assessed by, for example, radiolabeling either ubiquitin or ubiquitinated protein or LAPTM5.

Nucleic acids, such as DNA probes, comprising sequences of the gene can be used in a hybridization assay to detect the presence of hematopoietic cells in a sample. An example of such a method is set forth below.

Either DNA or RNA can be used in such an assay method. The DNA which can be used in the method can be cDNA or genomic DNA. The source of DNA can be from any cell or cells removed from the individual and can include cultured progeny thereof, such as somatic cells, blood cells, sperm, fibroblasts or other somatic or germline cells. Also, because the nucleic acid which is preferably analyzed is native or germline DNA, the method can be carried out prior or subsequent to onset of any particular disease or disease symptoms. Where cDNA or RNA is to be used, the nucleic acid source should be from hematopoietic cells.

The assay can be conducted using methods generally known in the art, such as by PCR (exemplified herein below). In yet another embodiment, the protein encoded by the DNA can be identified, such as with an antibody which selectively binds to one or more epitopes of the protein.

As such, the invention further relates to the preparation of antibodies which selectively bind the LAPTM5 protein or an antigenic or immunogenic fragment thereof. The antibodies can be polyclonal, monoclonal, chimeric or humanized. Suitable methods for making these products are well known to the person of ordinary skill in the art. The antibodies, in addition to selectively binding the protein, can optionally also possess the ability to block one or more biological functions of the protein, such as the ability to bind to ubiquitin. Such an antibody possesses an additional advantage of being useful to further study the function of the protein in the cell.

The antibodies can also be useful in the detection of hematopoietic cells or hematopoietic lysosomes in a sample. For example, the method comprises contacting the sample with the antibody under conditions sufficient for the antibody to bind to the LAPTM5 protein and detecting the presence of bound antibody. It may be necessary, in such an assay, to lyse the cells to expose the proteins. In yet another embodiment, the antibody can be used as a marker for lysosomal proteins, as also exemplified herein.

The present invention will now be illustrated by the following examples, which are not intended to be limiting in any way.

EXEMPLIFICATION

Cell Lines and Primary Cells

Hematopoietic cell lines used included erythroleukemia (K562, OCIR, OCI-M2, HEL), myeloblastic (KG-1), promyelocytic (HL60), T-cell leukemia (Molt-4), T-cell (DU528), B-cell (Nalm-6), myeloma (My-1), megakaryocytic (Dami), and mast cell (HMC-1). Nonhematopoietic cell lines used were bone marrow stromal (BS-1, L88), hepatoma (Hep G2), lung cancer (Calu-1), melanoma (HS294, SKMEL), cervical cancer (HeLa), skeletal muscle (HuSK), neuroblastoma (SKNH), and prostate cancer (PC3). All cell lines were maintained in Iscove's modified Dulbecco's medium supplemented with 10% fetal calf serum and 1 mM L-glutamine.

Northern and Southern Analysis

Standard procedures for nucleic acid analysis were carried out following established protocols (Sambrook, J. et al., "Molecular Cloning: A Laboratory Manual," 2nd ed., Cold Spring Harbor Laboratory Press, Plainview, N.Y. (1989)).

Identifying and Isolating cDNA

Subtractive hybridization was carried out between hematopoietic cell lines (K562, KG-1, and DU528) and a nonhematopoietic bone marrow-derived stromal line (BS-1) to construct subtractive cDNA libraries as described (Lelias, J- M. ct al., *Proc. Natl. Acad. Sci. USA* 90:1479–1483 (1993). cDNA inserts released from hematopoietic (DU528/BS-1 and KG-1/BS-1) and nonhematopoietic (BS-1/BS-1) subtractive libraries were used to screen the K562/BS-1 library. Clones differentially hybridized by hematopoietic probes were isolated, and the cDNAs were used for further cloning of full-length cDNAs and expression studies.

By differential screening of the K562 cDNA library with cDNA probes from two hematopoietic libraries (enriched for hematopoietic cDNAs) and cDNA probes from the nonhematopoietic BS-1 library, clones hybridizing only to hematopoietic probes were isolated. One of these clones, denoted HS1.6, was then used to probe Northern filters of total RNA from hematopoietic and nonhematopoietic cells.

HS1.6 was used to probe total RNA in human hematopoietic and nonhematopoietic cells and primary bone marrow (BM) cells. Specifically, total RNA (15 µg/lane), resolved and transferred to Hybond-N filter (Amersham), was hybridized with $^{32}$P-labeled human HS1.6 cDNA and washed with 0.2× standard saline citrate (SSC) at 65° C. before autoradiography. HS1.6 detects a 2.3-kb transcript in lineages of erythroid (K562, OCIR, HEL), myeloid (KG-1, HL60), and lymphoid cell lineages (My-1, MOLT-4) and normal bone marrow (BM). II contrast, none of the nonhematopoietic cell lines representative of cells of ectodermal, endodermal, or mesodermal origin contained the transcript.

The HS1.6 cDNA was also used to probe total RNA from normal murine tissues. Northern analysis was performed in murine hematopoietic and nonhematopoietic tissues. As described above, RNA resolved and transferred onto a filter, and was probed with human HS1.6 cDNA and washed with 0.5× SSC at 50° C. before autoradiography. The mRNA is detected in hematopoietic tissues including spleen, bone marrow, thymus, and lymph nodes. In nonhematopoietic cells no transcripts were detectable.

To increase sensitivity for detection of gene expression, a filter of poly(A)$^+$ mRNA from human tissues (Clontech, Palo Alto) was probed with HS1.6. Northern filters of LAPTM5 in poly(A)$^+$ mRNA (2 µg/lane) from normal human tissues were probed with $^{32}$P-labeled human HS1.6 cDNA and washed with 0.2× SSC at 65° C. before autoradiography. This revealed a high level of the mRNA in peripheral blood leukocytes (PBL), thymus, and spleen. Lung tissue also contains a high level of the mRNA, while a much lower level of transcript was detected in placenta, liver, and kidney. In all other nonhematopoietic tissues the mRNA was absent or barely detectable.

Cloning and Structural Analysis of Full-Length cDNA

Clone HS1.6 was used to probe a normal human spleen cDNA library, and several longer cDNA clones were obtained and sequenced. The longest 2232-nucleotide-long human cDNA contains an open reading frame beginning with an initiator methionine at nucleotide 76 and ending with a stop codon at nucleotide 862 (FIG. 1). There is a long 3'-untranslated region. The predicted first methionine is defined by a good fit with the Kozak's consensus sequence ACC<u>A</u>TGG (Kozak, M. *Cell* 44:283–292 (1986)). No stop codon is seen upstream of the first ATG. To ensure that the cDNA represents the complete protein, additional cDNA fragments from the 5' region were derived from three different hematopoietic cDNA libraries (HL60 cell line, spleen, bone marrow) using PCR technique. A 3' PCR primer was made against the 5' region of the longest cDNA around the first ATG, while a 5' PCR primer was synthesized to recognize a region in the common cloning vector close to the cloning sites. At least three cDNA fragments from each of the three different hematopoietic cDNA libraries obtained by PCR amplification were sequenced. None of the clones revealed evidence of another putative ATG start site upstream of the one defined above. Thus, the long open reading frame predicts a protein of 262 amino acids. A Kyte-Doolittle hydrophobicity plot (Kyte, J. and Doolittle, R. F., *J. Mol. Biol.* 157:105–132 (1982)) identified five hydrophobic domains between hydrophilic amino and carboxyl ends (FIG. 2). A search of the GenBank database revealed no significant homology to any currently known proteins. The carboxyl-terminal end contains a proline-rich domain, PXXXPXXXPXPPP (SEQ ID NO:6).

Isolation of Murine cDNA

The 5' end of the human HS1.6 cDNA was next used to screen a murine Day 13 embryo cDNA library. Three positive clones were isolated, and the longest cDNA was sequenced together with partial sequence of the other clones to confirm accuracy of the nucleotide sequence obtained. The full-length murine cDNA is about 82% identical with the human cDNA, and at the amino acid level, both species share about 90% identity (FIG. 2). There is also no evidence of another ATG site upstream of the murine initiating codon. Residues in all five transmembrane domains and the proline-rich region in the carboxyl tail are highly conserved between the human and the murine proteins.

Embryos and In Vitro Culture of Yolk Sac Cells

Murine embryos from a pregnant female at Day 11 postcoitus (p.c.) were microdissected and separated into heads, livers, heart, and body remnants. Total RNA was extracted using RNAzol (Biotecx). Day 9.5 p.c. embryonic yolk sac cells were dissected and pooled from about 15 embryos by rnicrodissection. A portion (approximately ½) was used for extraction of total RNA, and the rest were cultured as described (Wong, P. M. C. et al., *Proc. Natl. Acad. Sci. USA* 83:3851–3854 (1986); Adra, C. N. et al., *Genes Chromosomes Cancer* 8:253–261 (1993)) supplemented with 1% deionized bovine serum albumin, 30% fetal calf serum, 0.1 mM 2-mercaptoethanol, 2 mM L-glutamine, 2 units/ml erythropoietin, murine stem cell factor (SCF, 50 ng/ml), and 5% pokeweed mitogen-stimulated spleen conditioned medium. Culture plates were seeded at $5 \times 10^4$ cells per milliliter, and developing colonies were harvested and pooled at Days 2.5, 4, and 6.

The colonies include those containing only erythroid, macrophage, and granulocytic cells and those with mixed lineages. The RNA was used to prepare a Northern blot and probed sequentially with the murine homologue of HS1.6 and a cDNA probe for embryonic globin, βh1. The blots revealed that the mRNA for murine HS1.6 was detected in undifferentiated Day 9.5 yolk sac cells at a very low level in contrast to the very high level of embryonic globin mRNA. Upon differentiation into hematopoietic colonies there was a dramatic increase in the level of HS1.6 mRNA by Day 2.5, and the level remained essentially the same in colonies from subsequent days.

To examine if the same preferential expression of the gene in hematopoietically active adult tissues could be seen in embryonic tissues, a Northern blot was prepared consisting of total RNA from CCE murine embryonal stem (ES) cells (Wulf, G. M. et al., EMBO J. 12:5065–5074 (1993)) and total RNA (20 μg/lane) extracted from the head, liver, heart, and body remnant of Day 11 p.c. murine embryos. The filter was hybridized with the murine homologue for HS1.6. Unlike adult tissues, the mRNA could be detected in all tissues at about equal levels, with an even higher level of expression in ES cells.

Generation of Antibody

A peptide, CSKTPEGGPAPPPYSEV (the "SKTP peptide")(SEQ ID NO:5), from the carboxyl terminus was synthesized (Quality Control Biotechnology, Hopkinton) with the amino-terminal cysteine added to facilitate purification procedures. The antigen was suspended in saline and emulsified in Freund's adjuvant before injection subcutaneously into 3- to 9-month-old NZB rabbits to raise antiserum following established protocols (Harlow, E. and Lane, D., "Antibodies: A Laboratory Manual," pp. 53–138, Cold Spring Harbor Laboratory, Cold Spring Harbor, N.Y. (1988)).

Cells obtained from hematopoietic and nonhematopoietic cell lines, growing in log phase were lysed in buffer (20 mM Tris, 137 mM NaCl, 10% glycerol, 1% NP-40, 10 mM EDTA, 100 mM NaF) in the presence of protease inhibitors, and cleared lysates were analyzed in Western blots following standard protocols using the antibody at 1:500 dilution.

Western analysis of lysates from a spectrum of hematopoietic and nonhematopoietic cell lines, described above, with the antibody revealed a 29-kDa protein only in hematopoietic cells. Specificity of the detected protein was confirmed by (i) the specific detection of the protein only in cell lines positive for the HS1.6 mRNA and (ii) the elimination of the 29-kDa band after competitive absorption of the antiserum with the immunizing SKTP peptide used at 12 μg/ml. No higher molecular weight protein species was detected. Lower molecular weight peptides from degradation of the protein were observed as well, indicating that the protein may not be very stable under these conditions.

Immunofluorescence Studies

Adherent cells were cultured on coverslips to 80% confluence while nonadherent hematopoietic cells were prepared as cytospin. Cells were fixed with 3% formaldehyde in phosphate-buffered saline (PBS) and permeabilized in 0.2% NP-40 in PBS. All subsequent washes and antibody hybridization were carried out in the presence of NP-40/PBS buffer. Cells were prehybridized with 10% skim milk before reacting with antibodies. Monoclonal antibodies used for staining lysosomes and golgi were H4A3, H4B4, H15C6, and AD7 against LAMP-1 (Chen, J. W. et al., J. Biol. Chem. 263:8754–8758 (1988)), LAMP-2 (Cha, Y. et al., J. Biol. Chem. 265:5008–5013 (1990)), CD63 (Metzelaar, M. J. et al., J. Biol. Chem. 266:3239–3245 (1991)), and golgi p200 (Narula, N. et al., J. Cell Biol. 117:27–38 (1992)), respectively. These monoclonal antibodies were used at 1:300 dilution and the SKTP antiserum at 1:2000 dilution. Second antibodies were goat anti-rabbit or anti-murine immunoglobulin conjugated to either TRITC or FITC (Jackson ImmunoResearch Lab, PA.).

Lysosomes and other cellular fractions were isolated from rat spleen as described for rat liver (Cuervo, A. M. et al., Eur. J. Biochem. 227:792–800 (1995)). Briefly, spleen homogenate from 20-h starved Wistar rats was centrifuged at 600 g to obtain nuclear pellet. Supernatants were then sedimented at 4300 g to separate mitochondria and at 17,000 g to obtain a light mitochondrial-lysosome fraction that was loaded onto the bottom of a discontinuous metrizamide gradient to separate lysosomes from light mitochondrias (Wattiaux, R. et al., J. Cell Biol. 78:349–368 (1978). Microsomes (in pellet) and cytosol (in supernatant) were obtained after centrifugation at 150,000 g for 1 hour in the supernatant from the mitochondrial-lysosomal fraction. Each fraction was resuspended in 0.25M sucrose.

Immunofluorescence staining of various cells with the anti-SKTP antiserum resulted in a prominent staining around nuclei. Intense staining with a mixture of punctate and linear patterns was seen in a perinuclear crescent with some fainter diffuse punctate staining beyond the perinuclear region. No definitive staining was observed in the plasma membrane. mRNA-positive cells stained positive with the antibody, while no other transcript-negative cells showed any immunofluorescent staining. Furthermore, the staining pattern is very similar for different lineages, including undifferentiated ES cells. To confirm the specificity of the staining, competitive binding with the immunizing peptide was carried out. Preincubation of the anti-SKTP serum with SKTP peptide (12 μg/ml) completely eliminated immunofluorescent staining of positive cells, whereas preincubation with an irrelevant peptide gave the same intensity of positive staining as with the untreated antibody. Two-color staining with the antibody and a monoclonal antibody, AD7, against the golgi p200 protein (Narula, N. et al., J. Cell Biol. 117:27–38 (1992)) revealed that the HS1.6 protein (fluorescent green) was distributed around the TRITC-labeled golgi apparatus. Further simultaneous staining with the anti-SKTP serum and three monoclonal antibodies against lysosomal proteins, LAMP-1 (Chen, J. W. et al., J. Biol. Chem. 263:8754–8759 (1988)), LAMP-2 (Cha, Y. et al., J. Biol. Chem. 265:5008–5013 (1990), and CD63 (Metzelaar, M. J. et al., J. Biol. Chem. 268:3239–3245 (1991)), revealed that the protein colocalized closely with lysosomes. Staining of lysosomes in HEL cells by anti-LAMP-1 antibody, revealed by red TRITC, gave an intense punctate pattern in a perinuclear crescent. The same cells double stained with anti-SKTP serum, revealing the HS1.6-encoded protein with green fluorescence, showed a pattern of distribution identical to that of LAMP-1. Because of the localization of the protein to the lysosome organelle and the predicted 5-transmembrane structure of the protein, the protein was named lysosome-associated protein, transmembrane-5 (LAPTM5).

As discussed above, different subcellular fractions from rat spleens enriched for nuclei, mitochondria, light mitochondria, lysosomes, and microsomes were prepared by differential centrifugation and discontinuous gradient of metrizamide. In the first experiment, 75 μg of proteins from each fraction was separated by SDS/PAGE and immunoblotted with specific antibody against LAPTM5 protein and the chemoluminescent (ECL, Amersham) method of detection was used. In the second experiment, 150 μg of cellular fractions was loaded and the second antibody was alkaline phosphatase-conjugated goat anti—rabbit antiserum. Western blots were prepared and probed with the anti-SKTP antiserum. A 29-kDa/LAPTM5 protein, similar to that seen in total cell lysate, is consistently detected in lysosomal fraction. The overall weak signal is most likely because an anti-human protein serum was used against rat subcellular fractions. No protein is detected in the nucleus or the mitochondria fraction. The 29-kDa protein is sometimes detected in lower amounts in homogenate and in the microsome fraction, possibly due to contamination by endosomes.

Chromosomal Localization of LAPTM5 by Fluorescence In Situ Hybridization

The fluorescence in situ hybridization (FISH) technique was used to determine the subchromosomal location of LAPTM5 as described (Adra, C. N. et al., *Genomics* 24:188–190 (1994)). Human metaphases were prepared from phytohemagglutinin-stimulated peripheral lymphocytes. The LAPTM5 cDNA was labeled by nick-translation with biotin-11-UTP (Enzo Diagnostics). The labeled probe was hybridized to metaphase cells and detected by fluorescein-conjugated avidin (Vector Laboratories). Slides were examined by two blind observers.

Thirty-eight chromosomes from 31 metaphases were scored for the positive chromosomal band. Band 1p34 was labeled on all 38 chromosomes, 4 as singlets and 34 as doublets. No signal was detected on other chromosomes in these cells or on other bands on chromosome 1. Therefore LAPTM5 is localized to chromosome 1p34.

Equivalents

Those skilled in the art will know, or be able to ascertain, using no more than routine experimentation, many equivalents to the specific embodiments of the invention described herein. These and all other equivalents are intended to be encompassed by the following claims.

We claim:

1. An isolated nucleic acid consisting of the sequence set forth as SEQ ID NO: 1.

2. A plasmid comprising:

(a) an isolated nucleic acid encoding LAPTM5 that specifically hybridizes under stringent conditions to the complement of the sequence set forth as SEQ ID NO: 1, said isolated nucleic acid comprising a DNA sequence having the sequence set forth as SEQ ID NO: 1; and (b) a promoter sequence operably linked to said nucleic acid.

3. A nucleic acid that specifically hybridizes under stringent conditions to the sequence set forth as SEQ ID NO: 1, comprising the full length complement of the sequence set forth as SEQ ID NO: 1.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 2226 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 76..861

(xi) SEQUENCE DESCRIPTION: SEQ ID NO:1:

```
CTTCCCCTTC TCTGCCCTGC TCCAGGCACC AGGCTCTTTC CCCTTCAGTG TCTCAGAGGA        60

GGGGACGGCA GCACC ATG GAC CCC CGC TTG TCC ACT GTC CGC CAG ACC TGC       111
                Met Asp Pro Arg Leu Ser Thr Val Arg Gln Thr Cys
                  1               5                  10

TGC TGC TTC AAT GTC CGC ATC GCA ACC ACC GCC CTG GCC ATC TAC CAT         159
Cys Cys Phe Asn Val Arg Ile Ala Thr Thr Ala Leu Ala Ile Tyr His
            15                  20                  25

GTG ATC ATG AGC GTC TTG TTG TTC ATC GAG CAC TCA GTA GAG GTG GCC         207
Val Ile Met Ser Val Leu Leu Phe Ile Glu His Ser Val Glu Val Ala
        30                  35                  40

CAT GGC AAG GCG TCC TGC AAG CTC TCC CAG ATG GGC TAC CTC AGG ATC         255
His Gly Lys Ala Ser Cys Lys Leu Ser Gln Met Gly Tyr Leu Arg Ile
 45                  50                  55                  60

GCT GAC CTG ATC TCC AGC TTC CTG CTC ATC ACC ATG CTC TTC ATC ATC         303
Ala Asp Leu Ile Ser Ser Phe Leu Leu Ile Thr Met Leu Phe Ile Ile
                        65                  70                  75

AGC CTG AGC CTA CTG ATC GGC GTA GTC AAG AAC CGG GAG AAG TAC CTG         351
Ser Leu Ser Leu Leu Ile Gly Val Val Lys Asn Arg Glu Lys Tyr Leu
                80                  85                  90
```

```
                                                                -continued

CTG CCC TTC CTG TCC CTG CAA ATC ATG GAC TAT CTC CTG TGC CTG CTC           399
Leu Pro Phe Leu Ser Leu Gln Ile Met Asp Tyr Leu Leu Cys Leu Leu
         95                  100                 105

ACC CTG CTG GGC TCC TAC ATT GAG CTG CCC GCC TAC CTC AAG TTG GCC           447
Thr Leu Leu Gly Ser Tyr Ile Glu Leu Pro Ala Tyr Leu Lys Leu Ala
    110                 115                 120

TCC CGG AGC CGT GCT AGC TCC TCC AAG TTC CCC CTG ATG ACG CTG CAG           495
Ser Arg Ser Arg Ala Ser Ser Ser Lys Phe Pro Leu Met Thr Leu Gln
125                 130                 135                 140

CTG CTG GAC TTC TGC CTG AGC ATC CTG ACC CTC TGC AGC TCC TAC ATG           543
Leu Leu Asp Phe Cys Leu Ser Ile Leu Thr Leu Cys Ser Ser Tyr Met
                145                 150                 155

GAA GTG CCC ACC TAT CTC AAC TTC AAG TCC ATG AAC CAC ATG AAT TAC           591
Glu Val Pro Thr Tyr Leu Asn Phe Lys Ser Met Asn His Met Asn Tyr
            160                 165                 170

CTC CCC AGC CAG GAG GAT ATG CCT CAT AAC CAG TTC ATC AAG ATG ATG           639
Leu Pro Ser Gln Glu Asp Met Pro His Asn Gln Phe Ile Lys Met Met
        175                 180                 185

ATC ATC TTT TCC ATC GCC TTC ATC ACT GTC CTT ATC TTC AAG GTC TAC           687
Ile Ile Phe Ser Ile Ala Phe Ile Thr Val Leu Ile Phe Lys Val Tyr
    190                 195                 200

ATG TTC AAG TGC GTG TGG CGG TGC TAC AGA TTG ATC AAG TGC ATG AAC           735
Met Phe Lys Cys Val Trp Arg Cys Tyr Arg Leu Ile Lys Cys Met Asn
205                 210                 215                 220

TCG GTG GAG GAG AAG AGA AAC TCC AAG ATG CTC CAG AAG GTG GTC CTG           783
Ser Val Glu Glu Lys Arg Asn Ser Lys Met Leu Gln Lys Val Val Leu
                225                 230                 235

CCG TCC TAC GAG GAA GCC CTG TCT TTG CCA TCG AAG ACC CCA GAG GGG           831
Pro Ser Tyr Glu Glu Ala Leu Ser Leu Pro Ser Lys Thr Pro Glu Gly
            240                 245                 250

GGC CCA GCA CCA CCC CCA TAC TCA GAG GTG TGACCCTCGC CAGGCCCCAG             881
Gly Pro Ala Pro Pro Pro Tyr Ser Glu Val
        255                 260

CCCCAGTGCT GGGAGGGGTG GAGCTGCCTC ATAATCTGCT TTTTTGCTTT GGTGGCCCCT          941

GTGGCCTGGG TGGGCCCTCC CGCCCCTCCC TGGCAGGACA ATCTGCTTGT GTCTCCCTCG         1001

CTGGCCTGCT CCTCCTGCAG GGCCTGTGAG CTGCTCACAA CTGGGTCAAC GCTTTAGGCT         1061

GAGTCACTCC TCGGGTCTCT CCATAATTCA GCCCAACAAT GCTTGGTTTA TTTCAATCAG         1121

CTCTGACACT TGTTTAGACG ATTGGCCATT CTAAAGTTGG TGAGTTTGTC AAGCAACTAT         1181

CGACTTGATC AGTTCAGCCA AGCAACTGAC AAATCAAAAA CCCACTTGTC AGTTCAGTAA         1241

AATAATTTGG TCAAACAACA GTCTATTGCA TTGATTTATA AATAGTTGTC AGTTCACATA         1301

GCAATTTAAT CAAGTAATCA TTAATTAGTT ACCCCCTATA TATAAATATA TGTAATCAAT         1361

TTCTTCAAAT AGCTTGCTTA CATGATAATC AATTAGCCAA CCATGAGTCA TTTAGAATAG         1421

TGATAAATAG AATACACAGA ATAGTGATGA AATTCAATTT AAAAAATCAC GTTAGCCTCC         1481

AAACCATTTA ATTCAAATGA ACCCATCAAC TGGATGCCAA CTCTGGCGAA TGTAGGACCT         1541

CTGAGTGGCT GTATAATTGT TAATTCAAAT GAAATTCATT TAAACAGTTG ACAAACTGTC         1601

ATTCAACAAT TAGCTCCAGG AAATAACAGT TATTTCATCA TAAAACAGTC CCTTCAAACA         1661

CACAATTGTT CTGCTGAAGA GTTGTCATCA ACAATCCAAT GCTCACCTAT TCAGTTGCTC         1721

TGTGGTCAGT GTGGCTGCAT AGCAGTGGAT TCCATGAAAG GAGTCATTTT AGTGATGAGC         1781

TGCCAGTCCA TTCCCAGGCC AGGCTGTCGC TGGCCATCCA TTCAGTCGAT TCAGTCATAG         1841

GCGAATCTGT TCTGCCCGAG GCTTGTGGTC AAGCAAAAAT TCAGCCCTGA AATCAGGCAC         1901

ATCTGTTCGT TGGACTAAAC CCACAGGTTA GTTCAGTCAA AGCAGGCAAC CCCCTTGTGG         1961
```

```
GCACTGACCC TGCCACTGGG GTCATGGCGG TTGTGGCAGC TGGGGAGGTT TGGCCCCAAC    2021

AGCCCTCCTG TGCCTGCTTC CCTGTGTGTC GGGGTCCTCC AGGGAGCTGA CCCAGAGGTG    2081

GAGGCCACGG AGGCAGGGTC TCTGGGGACT GTCGGGGGGT ACAGAGGGAG AAGGCTCTGC    2141

AAGAGCTCCC TGGCAATACC CCCTTGTGTA ATTGCTTTGT GTGCGACAGG GAGGAAGTTT    2201

CAATAAAGCA ACAACAAGCT TCAAG                                          2226
```

(2) INFORMATION FOR SEQ ID NO:2:

(i) SEQUENCE CHARACTERISTICS:
        (A) LENGTH: 262 amino acids
        (B) TYPE: amino acid
        (D) TOPOLOGY: linear (ii) MOLECULE TYPE: protein (xi) SEQUENCE DESCRIPTION: SEQ ID NO:2:

```
Met Asp Pro Arg Leu Ser Thr Val Arg Gln Thr Cys Cys Cys Phe Asn
 1               5                  10                  15

Val Arg Ile Ala Thr Thr Ala Leu Ala Ile Tyr His Val Ile Met Ser
                20                  25                  30

Val Leu Leu Phe Ile Glu His Ser Val Glu Val Ala His Gly Lys Ala
            35                  40                  45

Ser Cys Lys Leu Ser Gln Met Gly Tyr Leu Arg Ile Ala Asp Leu Ile
    50                  55                  60

Ser Ser Phe Leu Leu Ile Thr Met Leu Phe Ile Ile Ser Leu Ser Leu
65                  70                  75                  80

Leu Ile Gly Val Val Lys Asn Arg Glu Lys Tyr Leu Leu Pro Phe Leu
                85                  90                  95

Ser Leu Gln Ile Met Asp Tyr Leu Leu Cys Leu Leu Thr Leu Leu Gly
            100                 105                 110

Ser Tyr Ile Glu Leu Pro Ala Tyr Leu Lys Leu Ala Ser Arg Ser Arg
        115                 120                 125

Ala Ser Ser Ser Lys Phe Pro Leu Met Thr Leu Gln Leu Leu Asp Phe
130                 135                 140

Cys Leu Ser Ile Leu Thr Leu Cys Ser Ser Tyr Met Glu Val Pro Thr
145                 150                 155                 160

Tyr Leu Asn Phe Lys Ser Met Asn His Met Asn Tyr Leu Pro Ser Gln
                165                 170                 175

Glu Asp Met Pro His Asn Gln Phe Ile Lys Met Met Ile Ile Phe Ser
            180                 185                 190

Ile Ala Phe Ile Thr Val Leu Ile Phe Lys Val Tyr Met Phe Lys Cys
        195                 200                 205

Val Trp Arg Cys Tyr Arg Leu Ile Lys Cys Met Asn Ser Val Glu Glu
    210                 215                 220

Lys Arg Asn Ser Lys Met Leu Gln Lys Val Val Leu Pro Ser Tyr Glu
225                 230                 235                 240

Glu Ala Leu Ser Leu Pro Ser Lys Thr Pro Glu Gly Gly Pro Ala Pro
                245                 250                 255

Pro Pro Tyr Ser Glu Val
            260
```

(2) INFORMATION FOR SEQ ID NO:3:

(i) SEQUENCE CHARACTERISTICS:
        (A) LENGTH: 1333 base pairs

-continued (B) TYPE: nucleic acid
(C) STRANDEDNESS: double
(D) TOPOLOGY: linear (ii) MOLECULE TYPE: cDNA (ix) FEATURE:
    (A) NAME/KEY: CDS
    (B) LOCATION: 58..840

(xi) SEQUENCE DESCRIPTION: SEQ ID NO:3:

```
CGGTGCTTTG GGCCCAAGAC TCCTTACTCA GAGCCTCCGA AGAGGGGACT GCGCACC          57

ATG GCC TCC CGT GCA GCG CCG GTC AGA CAG ACA TGC TGT TGT TTC AAC        105
Met Ala Ser Arg Ala Ala Pro Val Arg Gln Thr Cys Cys Cys Phe Asn
 1               5                  10                  15

ATC CGA GTC GCC ACC ATA GCC CTG GCC ATT TAC CAC ATA GTC ATG AGT        153
Ile Arg Val Ala Thr Ile Ala Leu Ala Ile Tyr His Ile Val Met Ser
                20                  25                  30

GTC CTG CTG TTC ATT GAG CAT GTG GTG GAG GTG GCC CGC GGT AAA GTG        201
Val Leu Leu Phe Ile Glu His Val Val Glu Val Ala Arg Gly Lys Val
        35                  40                  45

TCC TGT AGG TTC TTC AAG ATG CCG TAC CTC AGG ATG GCT GAC CTG CTC        249
Ser Cys Arg Phe Phe Lys Met Pro Tyr Leu Arg Met Ala Asp Leu Leu
    50                  55                  60

TCC AGC TTC CTG CTC ATT GGC GTG CTC TTC ATC ATC AGC ATC AGC CTG        297
Ser Ser Phe Leu Leu Ile Gly Val Leu Phe Ile Ile Ser Ile Ser Leu
65                  70                  75                  80

CTG TTC GGC GTG GTC AAG AAC CGG GAG AAG TAC CTG ATA CCC TTC CTG        345
Leu Phe Gly Val Val Lys Asn Arg Glu Lys Tyr Leu Ile Pro Phe Leu
                85                  90                  95

TCC CTT CAA ATC ATG GAC TTC CTG CTC TGC CTG CTC ACA CTG CTG GGC        393
Ser Leu Gln Ile Met Asp Phe Leu Leu Cys Leu Leu Thr Leu Leu Gly
            100                 105                 110

TCC TAC ATC GAA TTG CCA GCG TAC TTG AAG CTT GCC CGG CCC CGG CCT        441
Ser Tyr Ile Glu Leu Pro Ala Tyr Leu Lys Leu Ala Arg Pro Arg Pro
        115                 120                 125

GGT CCT TCT AAG GTC CCC TTG ATG ACA CTG CAG CTG CTA GAC TTC TGT        489
Gly Pro Ser Lys Val Pro Leu Met Thr Leu Gln Leu Leu Asp Phe Cys
    130                 135                 140

TTG AGT ATC CTG ACC CTG TGC AGC TCC TAC ATG GAA GTG CCC ACC TAC        537
Leu Ser Ile Leu Thr Leu Cys Ser Ser Tyr Met Glu Val Pro Thr Tyr
145                 150                 155                 160

CTC AAC TTC AAG TCC ATG AAC CAC ATG AAT TAC CTC CCA AGC CAG GAG        585
Leu Asn Phe Lys Ser Met Asn His Met Asn Tyr Leu Pro Ser Gln Glu
                165                 170                 175

GGT GTG CCG CAC AGC CAG TTC ATC AAC ATG ATG CTC ATC TTC TCA GTG        633
Gly Val Pro His Ser Gln Phe Ile Asn Met Met Leu Ile Phe Ser Val
            180                 185                 190

GCC TTT ATC ACC GTG CTC ATC CTG AAG GTC TAC ATG TTC AAG TGT GTG        681
Ala Phe Ile Thr Val Leu Ile Leu Lys Val Tyr Met Phe Lys Cys Val
        195                 200                 205

TAC ACA TGC TAC AAA TTC TTG AAG CAC ATG AAT TCG GCC ATG GAG GAC        729
Tyr Thr Cys Tyr Lys Phe Leu Lys His Met Asn Ser Ala Met Glu Asp
    210                 215                 220

AGC AGC TCC AAG ATG TTC CTC AAG GTG GCT CTG CCG TCC TAC GAG GAA        777
Ser Ser Ser Lys Met Phe Leu Lys Val Ala Leu Pro Ser Tyr Glu Glu
225                 230                 235                 240

GCC TTG TCT CTG CCC CCT AAG ACT CCA GAG GGG GAC CCT GCA CCA CCC        825
Ala Leu Ser Leu Pro Pro Lys Thr Pro Glu Gly Asp Pro Ala Pro Pro
                245                 250                 255

CCA TAC TCA GAA GTG TGATCCCCAC CAGGCCTTTA GCCCTTGGGC TGGGAGAGGC        880
```

```
Pro Tyr Ser Glu Val
            260
```

| | |
|---|---:|
| AGAACTTCCT CCTCCTGCTT CTTCACTTTG GTGGTTGCTG TGGCCTGCCT GCTACAGGAC | 940 |
| AATCTGCTTG TGCCCCCCCT CACTGTCCTC TCCTCTCGGG GACCCCTCAC TCACAACTGA | 1000 |
| GTCACCCTGG GCTCAGTGAC CCTTTGCGGC TCAGGATACT CAGCCTAGCA GCCCGTCTCG | 1060 |
| TCTCCATCAG CAGTGACACT TGTTCAGAGC GCAGCCATAG GAAGTTAGGG TGCGTTTGGT | 1120 |
| TAACAGCTAC CGGCTTGATC TGTTTGGCCA GGCAGCAGCA GGAAGAGAAT CTGGCCAAGC | 1180 |
| AATAGTTCCT GGTGTCAGTT TATACTCAGC TGTCAGACGA CAGGATGGGT CATGATTGTG | 1240 |
| GTGCCCGTTT GCCACCTCCA GTACCCCAAA AGTGTACAAA CAAAACAATT CCTTCAAATA | 1300 |
| GCTTGCTTAA ATAGCGATTC AGCCCCGGAA TTC | 1333 |

(2) INFORMATION FOR SEQ ID NO:4:

(i) SEQUENCE CHARACTERISTICS:
        (A) LENGTH: 261 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

```
Met Ala Ser Arg Ala Ala Pro Val Arg Gln Thr Cys Cys Phe Asn
1               5                  10                  15

Ile Arg Val Ala Thr Ile Ala Leu Ala Ile Tyr His Ile Val Met Ser
                20                  25                  30

Val Leu Leu Phe Ile Glu His Val Val Glu Val Ala Arg Gly Lys Val
            35                  40                  45

Ser Cys Arg Phe Phe Lys Met Pro Tyr Leu Arg Met Ala Asp Leu Leu
    50                  55                  60

Ser Ser Phe Leu Leu Ile Gly Val Leu Phe Ile Ile Ser Ile Ser Leu
65                  70                  75                  80

Leu Phe Gly Val Val Lys Asn Arg Glu Lys Tyr Leu Ile Pro Phe Leu
                85                  90                  95

Ser Leu Gln Ile Met Asp Phe Leu Leu Cys Leu Leu Thr Leu Leu Gly
            100                 105                 110

Ser Tyr Ile Glu Leu Pro Ala Tyr Leu Lys Leu Ala Arg Pro Arg Pro
        115                 120                 125

Gly Pro Ser Lys Val Pro Leu Met Thr Leu Gln Leu Leu Asp Phe Cys
    130                 135                 140

Leu Ser Ile Leu Thr Leu Cys Ser Ser Tyr Met Glu Val Pro Thr Tyr
145                 150                 155                 160

Leu Asn Phe Lys Ser Met Asn His Met Asn Tyr Leu Pro Ser Gln Glu
                165                 170                 175

Gly Val Pro His Ser Gln Phe Ile Asn Met Met Leu Ile Phe Ser Val
            180                 185                 190

Ala Phe Ile Thr Val Leu Ile Leu Lys Val Tyr Met Phe Lys Cys Val
        195                 200                 205

Tyr Thr Cys Tyr Lys Phe Leu Lys His Met Asn Ser Ala Met Glu Asp
    210                 215                 220

Ser Ser Ser Lys Met Phe Leu Lys Val Ala Leu Pro Ser Tyr Glu Glu
225                 230                 235                 240

Ala Leu Ser Leu Pro Pro Lys Thr Pro Glu Gly Asp Pro Ala Pro Pro
                245                 250                 255
```

```
Pro Tyr Ser Glu Val
          260

(2) INFORMATION FOR SEQ ID NO:5:

(i) SEQUENCE CHARACTERISTICS:
        (A) LENGTH: 17 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:5:

Cys Ser Lys Thr Pro Glu Gly Gly Pro Ala Pro Pro Tyr Ser Glu
1               5                   10                  15

Val (2) INFORMATION FOR SEQ ID NO:6:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

Pro Xaa Xaa Xaa Pro Xaa Xaa Xaa Pro Xaa Pro Pro Pro
1               5                   10
```